(12) United States Patent
Hamprecht et al.

(10) Patent No.: US 6,683,213 B1
(45) Date of Patent: Jan. 27, 2004

(54) SUBSTITUTED ANILINE COMPOUNDS

(75) Inventors: Gerhard Hamprecht, Weinheim (DE); Olaf Menke, Altleiningen (DE); Michael Puhl, Lampertheim (DE); Robert Reinhard, Ludwigshafen (DE); Ingo Sagasser, Dannstadt (DE); Cyrill Zagar, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,355

(22) PCT Filed: Mar. 31, 2000

(86) PCT No.: PCT/EP00/02901

§ 371 (c)(1), (2), (4) Date: Sep. 11, 2001

(87) PCT Pub. No.: WO00/59868

PCT Pub. Date: Oct. 12, 2000

(30) Foreign Application Priority Data

Mar. 31, 1999 (DE) .......................................... 199 14 721

(51) Int. Cl.$^7$ ............................................. C07C 251/02
(52) U.S. Cl. ...................... 564/265; 558/411; 558/418; 558/425; 560/43
(58) Field of Search ................................. 558/411, 418, 558/425; 560/43; 564/265

(56) References Cited

U.S. PATENT DOCUMENTS 5,604,227 A * 2/1997 Bare et al. .................. 514/248

* cited by examiner

*Primary Examiner*—Shailendra Kumar
(74) *Attorney, Agent, or Firm*—Keil & Weinkauf

(57) ABSTRACT

The present invention relates to substituted aniline compounds of the formula 1

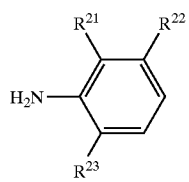

in which $R^{21}$, $R^{22}$ and $R^{23}$ have the meanings indicated in the description. The compounds according to the invention are intermediates for the preparation of herbicidally active pyridinedicarboxamide compounds.

6 Claims, No Drawings

SUBSTITUTED ANILINE COMPOUNDS

This application is a 371 of PCT/EP00/02901, filed Mar. 31, 2000.

The present invention relates to polysubstituted aniline compounds and to their use for the production of novel, herbicidally active compounds.

2-Aminobenzaldehyde O-methyloxime is known from Synthesis 1984, 266; it was prepared according to the methods described in Chem. Ber. 83, 78 (1950) and 34, 1330 (1901) and used for the synthesis of dihydroquinolinecarboxylic acid derivatives.

DE 1 231 709 shows a process for the preparation of o-aminobenzonitriles by thermolysis of β-isatin oximes. For example, 5-chloro- and 5-methyl-2-aminobenzonitrile are described, which can be used as intermediates for dyes, pesticides and therapeutics.

EP 32 672 A describes a process for the preparation of anthranilic acid esters by reaction of isatins with alcohols in the presence of hydrogen peroxide and alkali metal alkoxides. For example, the synthesis of methyl 3,5-dichloroanthranilate is discussed.

2,3,6-substituted anilines are described in Chem. Abstr. 73, 3578; 112, 5543; 78, 71690; 118, 147479; 70, 11553; 93, 71617; 121, 255784; 123, 313944; 76, 113245; 79, 146540; 128, 308308 and 131,129760.

The present invention relates to substituted anilines of the formula 1

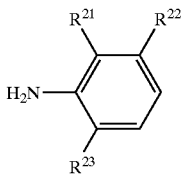

in which the variables $R^{21}$, $R^{22}$ and $R^{23}$ have the following meanings:

$R^{21}$ is $C_1-C_3$-alkoxymethyl, $C_1-C_3$-alkoximinomethyl, $C_1-C_3$-alkoxycarbonyl, $C_1-C_3$-alkylthiocarbonyl, $C(O)NH_2$, CN, Cl, Br, $C_1-C_3$-alkyl;

$R^{22}$ is Cl, Br, $C_1-C_3$-alkyl;

$R^{23}$ is hydrogen, $C_1-C_3$-alkoxymethyl, $C_1-C_3$-alkoxycarbonyl, $C_1-C_3$-alkylthiocarbonyl, $C(O)NH_2$, CN, Cl, Br, $C_1-C_3$-alkyl, $C_1-C_3$-alkoxy;

where
at least one of the radicals $R^{21}$ or $R^{23}$ is a group having a carbonyl group or a functional derivative thereof or is $C_1-C_3$-alkoxymethyl;

$R^{23}$ cannot be hydrogen nor can $R^{22}$ and $R^{23}$ have the same meaning if $R^{21}=C_1-C_3$-alkoxycarbonyl, $C_1-C_3$-alkylthiocarbonyl, $C(O)NH_2$ or CN;

$R^{22}$ does not have the same meaning as $R^{21}$ if $R^{21}$ is Cl, Br or $C_1-C_3$-alkyl and $R^{23}$ is $C_1-C_3$-alkoxycarbonyl and $R^{22}$ is not Cl if $R^{21}$ is $CH_3$ and $R^{23}$ is $C_1-C_3$-alkoxycarbonyl, if $R^{21}=C_1-C_3$-alkoxymethyl, $R^{23}$ is not hydrogen;

and the salts thereof.

Suitable salts are those with inorganic or organic acids. Suitable inorganic acids are, for example, hydrochloric acid, sulfuric acid, phosphoric acid, nitric acid etc. Suitable organic acids are, for example, acetic acid, citric acid, tartaric acid etc.

The organic moieties mentioned in the definition of $R^{21}$, $R^{22}$ and $R^{23}$ are collective terms for individual lists of the individual group members. All carbon chains, i.e. all alkyl moieties, can be straight-chain or branched.

The following are, for example:

$C_1-C_3$-alkoxymethyl: methoxymethyl, ethoxyethyl, n-propoxymethyl or 2-propoxymethyl, in particular 2-methoxymethyl;

$C_1-C_3$-alkoximinomethyl: methoximinomethyl, ethoximinomethyl, n-propoximinomethyl or 2-Propoximinomethyl, in particular methoximinomethyl;

$C_1-C_3$-alkoxycarbonyl: methoxycarbonyl, ethoxycarbonyl, n-propoxycarbonyl or 2-propoxycarbonyl, in particular methoxycarbonyl;

$C_1-C_3$-alkylthiocarbonyl: methylthiocarbonyl, ethylthiocarbonyl, n-propylthiocarbonyl or 2-propylthiocarbonyl, in particular methylthiocarbonyl;

$C_1-C_3$-alkyl: methyl, ethyl, n-propyl or 2-propyl, in particular methyl or ethyl;

$C_1-C_3$ alkoxy: methoxy, ethoxy, n-propoxy or 2-propoxy, in particular methoxy or ethoxy.

The groups having a carbonyl group or a functional derivative thereof are $C_1-C_3$-alkoxycarbonyl, $C_1-C_3$-alkylthiocarbonyl ($C_1-C_3$-alkyl-S—CO), $C(O)NH_2$, CN and $C_1-C_3$-alkoximinomethyl.

$R^{21}$ is preferably methoxymethyl, methoximinomethyl, ethoximinomethyl, methoxycarbonyl, ethoxycarbonyl, methylthiocarbonyl, CN, Cl, Br, methyl or ethyl;

$R^{22}$ is preferably Cl, Br, $CH_3$ or $C_2H_5$;

$R^{23}$ is preferably hydrogen, methoxymethyl, methoxycarbonyl, methylthiocarbonyl, CN, Cl, Br, methyl, ethyl, methoxy or ethoxy.

Preferred compounds of the formula 1 are those in which the variables have the following meanings:

A) $R^{21}$ is $C_1-C_3$-alkoxymethyl, $C_1-C_3$-alkoximinomethyl, $C_1-C_3$-alkoxycarbonyl, $C_1-C_3$-alkylthiocarbonyl, $C(O)NH_2$, Cl, Br, CN or $C_1-C_3$-alkyl;
$R^{22}$ is Cl, Br or $C_1-C_3$-alkyl and
$R^{23}$ is $C_1-C_3$-alkoxymethyl.

B) $R^{21}$ is $C_1-C_3$-alkoxymethyl or $C_1-C_3$-alkoximinomethyl;
$R^{22}$ is Cl, Br or $C_1-C_3$-alkyl and
$R^{23}$ is H, $C_1-C_3$-alkoxymethyl, $C_1-C_3$-alkylcarbonyl, $C_1-C_3$-alkylthiocarbonyl, $C(O)NH_2$, Cl, Br, $C_1-C_3$-alkyl or $C_1-C_3$-alkoxy, where $R^{23}$ cannot be H if $R^{21}$ is $C_1-C_3$-alkoxymethyl.

C) $R^{21}$ is $C_1-C_3$-alkoximinomethyl;
$R^{22}$ is Cl or Br;
$R^{23}$ is hydrogen, $C_1-C_3$-alkoxycarbonyl, $C_1-C_3$-alkoxy, $C(O)NH_2$, or cyano.

D) $R^{21}$ is $C_1-C_3$-alkoxycarbonyl, $C_1-C_3$-alkylthiocarbonyl, $C(O)NH_2$ or cyano;
$R^{22}$ and $R^{23}$, which are different from one another, are Cl, Br or $C_1-C_3$-alkyl, $R^{23}$ is furthermore $C_1-C_3$-alkoxycarbonyl, $C_1-C_3$-alkylthiocarbonyl or $C_1-C_3$-alkoxy.

E) $R^{21}$ and $R^{22}$ are Cl, Br or $C_1-C_3$-alkyl
$R^{23}$ is $C_1-C_3$-alkoxycarbonyl, $C_1-C_3$-alkylthiocarbonyl, $C_1-C_3$-alkoxymethyl or cyano, where in the two first-mentioned cases $R^{21}$ and $R^{22}$ do not have the same meanings.

F) $R^{21}$ is $C_1-C_3$-alkoxymethyl or $C_1-C_3$-alkoximinomethyl $R^{22}$ is Cl, Br or $C_1-C_3$-alkyl $R^{23}$ is $C_1-C_3$-alkoxycarbonyl, $C_1-C_3$-alkylthiocarbonyl, CN, $C_1-C_3$-alkyl or $C_1-C_3$-alkoxy.

The compounds of the formula 1 are intermediates for the preparation of the herbicidally active compounds of the formula A

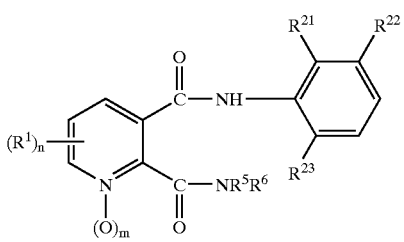

in which $R^{21}$, $R^{22}$ and $R^{23}$ have the meanings indicated above, $R^1$ is halogen, CN, $NO_2$, $C_1-C_3$-alkyl, $C_1-C_3$-haloalkyl, $C_1-C_3$-alkoxy, $C_1-C_3$-haloalkoxy, $C_1-C_3$-alkylthio, $C_1-C_3$-haloalkylthio, $C_1-C_3$-alkylsulfinyl, $C_1-C_3$-haloalkylsulfinyl, $C_1-C_3$-alkylsulfonyl, $C_1-C_3$-haloalkylsulfonyl, $C_3-C_6$-cycloalkyl, $C_3-C_6$-cycloalkyl-$C_1-C_3$-alkyl, $C_2-C_4$-alkenyl, $C_2-C_4$-haloalkenyl, $C_2-C_4$-alkynyl, $C_3-C_4$-haloalkynyl, amino, $C_1-C_3$-monoalkylamino or $C_1-C_3$-alkylcarbonyl;

$R^5$ is hydrogen, $C_1-C_3$-alkyl, OH or $C_1-C_4$-alkoxy;

$R^6$ is hydrogen, $C_1-C_6$-alkyl, $C_1-C_6$-haloalkyl, $C_1-C_6$-cyanoalkyl, $C_3-C_6$-cycloalkyl, $C_3-C_6$-cycloalkenyl, $C_3-C_6$-cycloalkyl-$C_1-C_3$-alkyl, $C_3-C_6$-cycloalkyl which has 1 or 2 substituents which independently of one another are selected from halogen or $C_1-C_3$-alkyl, $C_3-C_6$-cycloalkoxy-$C_1-C_3$-alkyl, $C_1-C_6$-Alkoxy-$C_1-C_6$-alkyl, $C_1-C_6$-alkylthio-$C_1-C_6$-alkyl, $C_1-C_6$-alkoxycarbonyl-$C_1-C_6$-alkyl, $C_3-C_6$-alkenyl, $C_3-C_6$-alkynyl, amino, $C_1-C_4$-monoalkylamino, di-$C_1-C_4$-alkylamino or $R^6$, together with $R^5$, is a 5- or 6-membered heterocycle which has 1, 2 or 3 heteroatoms, which independently of one another are selected from N, O and S, and optionally 1 or 2 substituents which independently of one another are selected from halogen or $C_1-C_3$-alkyl, $C_1-C_3$-alkoxy or $C_1-C_3$-haloalkyl;

m is 0 or 1 and n is 0, 1, 2 or 3. The compounds of the formula A are the subject of DE 199 14 721 of 31.3.1999.

Examples of preferred substituted anilines of the formula 1 are indicated in Table 1, in which $R^{21}$ to $R^{23}$ have the following meanings:

| No. | $R^{21}$ | $R^{22}$ | $R^{23}$ |
|---|---|---|---|
| 1 | CH=NOCH$_3$ | Cl | H |
| 2 | CH=NOCH$_3$ | Br | H |
| 3 | CH=NOCH$_3$ | CH$_3$ | H |
| 4 | CH=NOCH$_3$ | C$_2$H$_5$ | H |
| 5 | CH=NOCH$_3$ | Cl | CO$_2$CH$_3$ |
| 6 | CH=NOCH$_3$ | Br | CO$_2$CH$_3$ |
| 7 | CH=NOCH$_3$ | CH$_3$ | CO$_2$CH$_3$ |
| 8 | CH=NOCH$_3$ | Cl | CN |
| 9 | CH=NOCH$_3$ | Br | CN |
| 10 | CH=NOCH$_3$ | Cl | Cl |
| 11 | CH=NOCH$_3$ | Cl | Br |
| 12 | CH=NOCH$_3$ | Br | Cl |
| 13 | CH=NOCH$_3$ | Cl | C(O)NH$_2$ |
| 14 | CH=NOCH$_3$ | Cl | CH$_3$ |
| 15 | CH=NOCH$_3$ | Br | CH$_3$ |
| 16 | CH=NOCH$_3$ | CH$_3$ | CN |
| 17 | CH=NOCH$_3$ | CH$_3$ | Cl |
| 18 | CH=NOCH$_3$ | Cl | CH$_3$O |
| 19 | CH=NOCH$_3$ | Br | CH$_3$O |
| 20 | CH=NOCH$_3$ | Cl | C(O)SCH$_3$ |
| 21 | CH=NOCH$_3$ | Br | C(O)SCH$_3$ |
| 22 | CH=NOCH$_3$ | Cl | C$_2$H$_5$ |
| 23 | CH=NOCH$_3$ | Br | C$_2$H$_5$ |
| 24 | CH=NOC$_2$H$_5$ | Cl | H |
| 25 | CH=NOC$_2$H$_5$ | Br | H |
| 26 | CH=NOC$_2$H$_5$ | CH$_3$ | H |
| 27 | CH=NOC$_2$H$_5$ | C$_2$H$_5$ | H |
| 28 | CH=NOC$_2$H$_5$ | Cl | CO$_2$CH$_3$ |
| 29 | CH=NOC$_2$H$_5$ | Br | CO$_2$CH$_3$ |
| 30 | CH=NOC$_2$H$_5$ | CH$_3$ | CO$_2$CH$_3$ |
| 31 | CH=NOC$_2$H$_5$ | Cl | CN |
| 32 | CH=NOC$_2$H$_5$ | Br | CN |
| 33 | CH=NOC$_2$H$_5$ | Cl | Cl |
| 34 | CH=NOC$_2$H$_5$ | Cl | Br |
| 35 | CH=NOC$_2$H$_5$ | Br | Cl |
| 36 | CH=NOC$_2$H$_5$ | Cl | C(O)NH$_2$ |
| 37 | CH=NOC$_2$H$_5$ | Cl | CH$_3$ |
| 38 | CH=NOC$_2$H$_5$ | Br | CH$_3$ |
| 39 | CH=NOC$_2$H$_5$ | CH$_3$ | CN |
| 40 | CH=NOC$_2$H$_5$ | CH$_3$ | Cl |
| 41 | CH=NOC$_2$H$_5$ | Cl | CH$_3$O |
| 42 | CH=NOC$_2$H$_5$ | Br | CH$_3$O |
| 43 | CH=NOC$_2$H$_5$ | Cl | C(O)SCH$_3$ |
| 44 | CH=NOC$_2$H$_5$ | Br | C(O)SCH$_3$ |
| 45 | CH=NOC$_2$H$_5$ | Cl | C$_2$H$_5$ |
| 46 | CH=NOC$_2$H$_5$ | Br | C$_2$H$_5$ |
| 47 | CO$_2$CH$_3$ | Cl | Br |
| 48 | CO$_2$CH$_3$ | Cl | CH$_3$ |
| 49 | CO$_2$CH$_3$ | Br | Cl |
| 50 | CO$_2$CH$_3$ | CH$_3$ | Cl |
| 51 | CO$_2$CH$_3$ | CH$_3$ | Br |
| 52 | CO$_2$CH$_3$ | CH$_3$ | CO$_2$CH$_3$ |
| 53 | CO$_2$CH$_3$ | CH$_3$ | C(O)SCH$_3$ |
| 54 | CO$_2$CH$_3$ | Cl | CO$_2$CH$_3$ |
| 55 | CO$_2$CH$_3$ | Cl | OCH$_3$ |
| 56 | CO$_2$CH$_3$ | Cl | C(O)NH$_2$ |
| 57 | CO$_2$CH$_3$ | Cl | CN |
| 58 | CO$_2$CH$_3$ | Br | CO$_2$CH$_3$ |
| 59 | CO$_2$CH$_3$ | Br | C(O)SCH$_3$ |
| 60 | CO$_2$CH$_3$ | Br | OCH$_3$ |
| 61 | CO$_2$CH$_3$ | Br | C(O)NH$_2$ |
| 62 | CO$_2$CH$_3$ | Br | CN |
| 63 | CO$_2$CH$_3$ | Cl | C(O)SCH$_3$ |
| 64 | CO$_2$CH$_3$ | Br | CH$_3$ |
| 65 | CO$_2$CH$_3$ | Cl | C$_2$H$_5$ |
| 66 | CO$_2$CH$_3$ | Br | C$_2$H$_5$ |
| 67 | CO$_2$CH$_3$ | CH$_3$ | C(O)NH$_2$ |
| 68 | CO$_2$CH$_3$ | CH$_3$ | CN |
| 69 | CO$_2$CH$_3$ | Cl | OC$_2$H$_5$ |
| 70 | CO$_2$CH$_3$ | Br | OC$_2$H$_5$ |
| 71 | CO$_2$C$_2$H$_5$ | Cl | Br |
| 72 | CO$_2$C$_2$H$_5$ | Cl | CH$_3$ |
| 73 | CO$_2$C$_2$H$_5$ | Br | Cl |
| 74 | CO$_2$C$_2$H$_5$ | CH$_3$ | Cl |
| 75 | CO$_2$C$_2$H$_5$ | CH$_3$ | Br |
| 76 | CO$_2$C$_2$H$_5$ | CH$_3$ | CO$_2$CH$_3$ |
| 77 | CO$_2$C$_2$H$_5$ | CH$_3$ | C(O)SCH$_3$ |
| 78 | CO$_2$C$_2$H$_5$ | Cl | CO$_2$CH$_3$ |
| 79 | CO$_2$C$_2$H$_5$ | Cl | OCH$_3$ |
| 80 | CO$_2$C$_2$H$_5$ | Cl | C(O)NH$_2$ |
| 81 | CO$_2$C$_2$H$_5$ | Cl | CN |
| 82 | CO$_2$C$_2$H$_5$ | Br | CO$_2$CH$_3$ |
| 83 | CO$_2$C$_2$H$_5$ | Br | C(O)SCH$_3$ |
| 84 | CO$_2$C$_2$H$_5$ | Br | OCH$_3$ |

| No. | $R^{21}$ | $R^{22}$ | $R^{23}$ |
| --- | --- | --- | --- |
| 85 | $CO_2C_2H_5$ | Br | $C(O)NH_2$ |
| 86 | $CO_2C_2H_5$ | Br | CN |
| 87 | $CO_2C_2H_5$ | Cl | $C(O)SCH_3$ |
| 88 | $CO_2C_2H_5$ | Br | $CH_3$ |
| 89 | $CO_2C_2H_5$ | Cl | $C_2H_5$ |
| 90 | $CO_2C_2H_5$ | Br | $C_2H_5$ |
| 91 | $CO_2C_2H_5$ | $CH_3$ | $C(O)NH_2$ |
| 92 | $CO_2C_2H_5$ | $CH_3$ | CN |
| 93 | $CO_2C_2H_5$ | Cl | $OC_2H_5$ |
| 94 | $CO_2C_2H_5$ | Br | $OC_2H_5$ |
| 95 | $C(O)SCH_3$ | Cl | Br |
| 96 | $C(O)SCH_3$ | Cl | $CH_3$ |
| 97 | $C(O)SCH_3$ | Br | Cl |
| 98 | $C(O)SCH_3$ | $CH_3$ | Cl |
| 99 | $C(O)SCH_3$ | $CH_3$ | Br |
| 100 | $C(O)SCH_3$ | $CH_3$ | $CO_2CH_3$ |
| 101 | $C(O)SCH_3$ | $CH_3$ | $C(O)SCH_3$ |
| 102 | $C(O)SCH_3$ | Cl | $CO_2CH_3$ |
| 103 | $C(O)SCH_3$ | Cl | $OCH_3$ |
| 104 | $C(O)SCH_3$ | Cl | $C(O)NH_2$ |
| 105 | $C(O)SCH_3$ | Cl | CN |
| 106 | $C(O)SCH_3$ | Br | $CO_2CH_3$ |
| 107 | $C(O)SCH_3$ | Br | $C(O)SCH_3$ |
| 108 | $C(O)SCH_3$ | Br | $OCH_3$ |
| 109 | $C(O)SCH_3$ | Br | $C(O)NH_2$ |
| 110 | $C(O)SCH_3$ | Br | CN |
| 111 | $C(O)SCH_3$ | Cl | $C(O)SCH_3$ |
| 112 | $C(O)SCH_3$ | Br | $CH_3$ |
| 113 | $C(O)SCH_3$ | Cl | $C_2H_5$ |
| 114 | $C(O)SCH_3$ | Br | $C_2H_5$ |
| 115 | $C(O)SCH_3$ | $CH_3$ | $C(O)NH_2$ |
| 116 | $C(O)SCH_3$ | $CH_3$ | CN |
| 117 | $C(O)SCH_3$ | Cl | $OC_2H_5$ |
| 118 | $C(O)SCH_3$ | Br | $OC_2H_5$ |
| 119 | $C(O)NH_2$ | Cl | Br |
| 120 | $C(O)NH_2$ | Cl | $CH_3$ |
| 121 | $C(O)NH_2$ | Br | Cl |
| 122 | $C(O)NH_2$ | $CH_3$ | Cl |
| 123 | $C(O)NH_2$ | $CH_3$ | Br |
| 124 | $C(O)NH_2$ | $CH_3$ | $CO_2CH_3$ |
| 125 | $C(O)NH_2$ | $CH_3$ | $C(O)SCH_3$ |
| 126 | $C(O)NH_2$ | Cl | $CO_2CH_3$ |
| 127 | $C(O)NH_2$ | Cl | $OCH_3$ |
| 128 | $C(O)NH_2$ | Cl | $C(O)NH_2$ |
| 129 | $C(O)NH_2$ | Cl | CN |
| 130 | $C(O)NH_2$ | Br | $CO_2CH_3$ |
| 131 | $C(O)NH_2$ | Br | $C(O)SCH_3$ |
| 132 | $C(O)NH_2$ | Br | $OCH_3$ |
| 133 | $C(O)NH_2$ | Br | $C(O)NH_2$ |
| 134 | $C(O)NH_2$ | Br | CN |
| 135 | $C(O)NH_2$ | Cl | $C(O)SCH_3$ |
| 136 | $C(O)NH_2$ | Br | $CH_3$ |
| 137 | $C(O)NH_2$ | Cl | $C_2H_5$ |
| 138 | $C(O)NH_2$ | Br | $C_2H_5$ |
| 139 | $C(O)NH_2$ | $CH_3$ | $C(O)NH_2$ |
| 140 | $C(O)NH_2$ | $CH_3$ | CN |
| 141 | $C(O)NH_2$ | Cl | $OC_2H_5$ |
| 142 | $C(O)NH_2$ | Br | $OC_2H_5$ |
| 143 | CN | Cl | Br |
| 144 | CN | Cl | $CH_3$ |
| 145 | CN | Br | Cl |
| 146 | CN | $CH_3$ | Cl |
| 147 | CN | $CH_3$ | Br |
| 148 | CN | $CH_3$ | $CO_2CH_3$ |
| 149 | CN | $CH_3$ | $C(O)SCH_3$ |
| 150 | CN | Cl | $CO_2CH_3$ |
| 151 | CN | Cl | $OCH_3$ |
| 152 | CN | Cl | $C(O)NH_2$ |
| 153 | CN | Cl | CN |
| 154 | CN | Br | $CO_2CH_3$ |
| 155 | CN | Br | $C(O)SCH_3$ |
| 156 | CN | Br | $OCH_3$ |
| 157 | CN | Br | $C(O)NH_2$ |
| 158 | CN | Br | CN |
| 159 | CN | Cl | $C(O)SCH_3$ |
| 160 | CN | Br | $CH_3$ |
| 161 | CN | Cl | $C_2H_5$ |
| 162 | CN | Br | $C_2H_5$ |
| 163 | CN | $CH_3$ | $C(O)NH_2$ |
| 164 | CN | $CH_3$ | CN |
| 165 | CN | Cl | $OC_2H_5$ |
| 166 | CN | Br | $OC_2H_5$ |
| 167 | Cl | Br | $CO_2CH_3$ |
| 168 | Br | Cl | $CO_2CH_3$ |
| 169 | Cl | $CH_3$ | $CO_2CH_3$ |
| 170 | Br | $CH_3$ | $CO_2CH_3$ |
| 171 | Cl | Br | $C(O)SCH_3$ |
| 172 | Br | Cl | $C(O)SCH_3$ |
| 173 | $CH_3$ | Br | $CO_2CH_3$ |
| 174 | $CH_3$ | Br | $C(O)SCH_3$ |
| 175 | $CH_3$ | Cl | $C(O)SCH_3$ |
| 176 | $C_2H_5$ | Cl | $CO_2CH_3$ |
| 177 | $C_2H_5$ | Br | $CO_2CH_3$ |
| 178 | $CH_3$ | Cl | $C(O)NH_2$ |
| 179 | $CH_3$ | Br | $C(O)NH_2$ |
| 180 | $CH_3$ | $CH_3$ | CN |
| 181 | $C_2H_5$ | Cl | $C(O)NH_2$ |
| 182 | $C_2H_5$ | Br | $C(O)NH_2$ |
| 183 | $C_2H_5$ | Cl | $C(O)SCH_2$ |
| 184 | $CH_3$ | Cl | CN |
| 185 | $CH_3$ | Br | CN |
| 186 | $C_2H_5$ | Cl | CN |
| 187 | $C_2H_5$ | Br | CN |
| 188 | Cl | $CH_3$ | CN |
| 189 | Cl | Cl | CN |
| 190 | $C_2H_5$ | $CH_3$ | CN |
| 191 | $C_2H_5$ | Br | $C(O)SCH_3$ |
| 192 | $CH_3OCH_2$ | Cl | $CH_3$ |
| 193 | $CH_3OCH_2$ | $CH_3$ | Cl |
| 194 | $CH_3OCH_2$ | $CH_3$ | $CH_3$ |
| 195 | $CH_3OCH_2$ | Cl | Cl |
| 196 | $CH_3OCH_2$ | Br | $CH_3$ |
| 197 | $CH_3OCH_2$ | Cl | $C_2H_5$ |
| 198 | $CH_3OCH_2$ | Br | $C_2H_5$ |
| 199 | $CH_3$ | Cl | $CH_3OCH_2$ |
| 200 | $C_2H_5$ | Cl | $CH_3OCH_2$ |
| 201 | $CH_3$ | Br | $CH_3OCH_2$ |
| 202 | $C_2H_5$ | Br | $CH_3OCH_2$ |
| 203 | $CH_3OCH_2$ | $CH_3$ | $CO_2CH_3$ |
| 204 | $CH_3OCH_2$ | Cl | $CO_2CH_3$ |
| 205 | $CH_3OCH_2$ | Br | $CO_2CH_3$ |
| 206 | $CH_3OCH_2$ | Cl | $C(O)SCH_3$ |
| 207 | $CH_3OCH_2$ | Br | $C(O)SCH_3$ |
| 208 | $CH_3OCH_2$ | Cl | CN |
| 209 | $CH_3OCH_2$ | Br | CN |
| 210 | $CO_2CH_3$ | Cl | $CH_3OCH_2$ |
| 211 | $C(O)SCH_3$ | Cl | $CH_3OCH_2$ |
| 212 | CN | Cl | $CH_3OCH_2$ |
| 213 | CN | Br | $CH_3OCH_2$ |
| 214 | $CH_3OCH_2$ | Cl | $OCH_3$ |
| 215 | $CH_3OCH_2$ | Br | $OCH_3$ |
| 216 | $CH_3OCH_2$ | Cl | $OC_2H_5$ |

The anilines of the formula 1 can be prepared by one of the following processes. The isatoic anhydrides used here as starting substances and their preparation are known per se and described in the literature, e.g. Chem. Abstr. 75, 98482; 117, 233811; 125, 300514. 3-Chloro-6-methylisatoic anhydride is described in greater detail in the synthesis of the starting substances.

The substituted anilines of the general formula 1a, in which $R^{21}$ is a $C_1$–$C_3$-alkoximinomethyl radical, can be prepared by reacting, for example, a substituted o-nitrobenzaldehyde of the formula 2

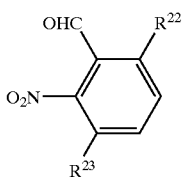

2 with hydroxylamine hydrochloride in the presence of a base and reacting the oxime of the formula 4 thus obtained

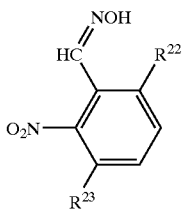

4 with an alkylating agent of the formula RG, in which R is a $C_1$–$C_3$-alkyl radical and G is a nucleophilically displaceable leaving group, in the presence of a base and reducing the oxime ether of the formula 6 thus obtained

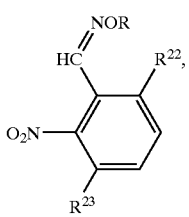

6 e.g. with iron in the presence of an acid or with hydrogen in the presence of a metal catalyst.

Examples of suitable, nucleophilically displaceable leaving groups are halogen, preferably chlorine, bromine or iodine, $C_1$–$C_3$-alkylsulfonyloxy such as methylsulfonyloxy, phenylsulfonyloxy, in which the phenyl radical can optionally be mono- or polysubstituted by halogen or $C_1$–$C_6$-alkyl, such as phenylsulfonyloxy, p-toluenesulfonyloxy or p-Cl-phenylsulfonyloxy or a $C_1$–$C_3$-dialkylsulfate, such as dimethyl- or diethylsulfate.

The oxime ether of the formula 6, however, can also be prepared by direct oximation of a substituted o-nitrobenzaldehyde 2 with a $C_1$–$C_3$-alkoxyamine of the formula 7

 7 or a salt thereof, e.g. the hydrochloride, in the presence of a base and then reducing to the aniline 1 as above.

The substituted anilines of the formula 1b, in which one of the radicals $R^{21}$ or $R^{23}$ is a carboxylic acid function, are likewise prepared by processes known per se, by converting, for example, a substituted aniline of the formula 8a or 8b

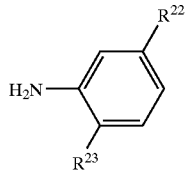

8a

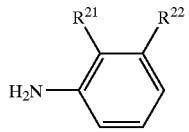

8b by means of chloral hydrate and hydroxylamine sulfate into the corresponding isonitrosoacetanilides of the formula 9a or 9b

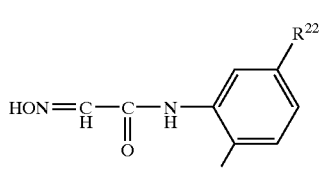

9a

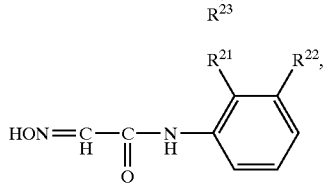

9b cyclizing these in the presence of an acid, e.g. sulfuric acid, to give the corresponding isatins of the formula 10a or 10b

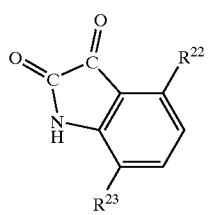

10a

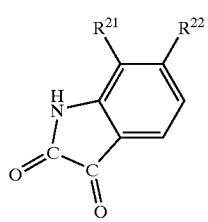

10b and reacting the latter with $C_1$–$C_3$-alkanols in the presence of alkali metal $C_1$–$C_3$-alkanolates and of aqueous hydrogen peroxide to give the corresponding anthranilic esters of the formula 13a or 13b.

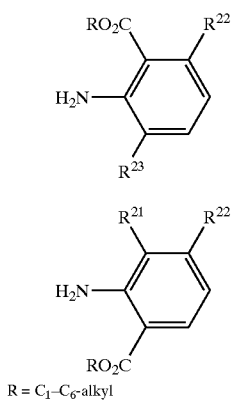

13a

13b

R = C₁–C₆-alkyl

By transesterification with higher alcohols or thiols, these can in turn be converted into corresponding longer-chain anthranilic esters or thioesters.

If the isatins of the formula 10a or 10b are reacted with hydroxylamine as for the oximes 4, the isatin β-oximes of the formula 14a or 14b are obtained

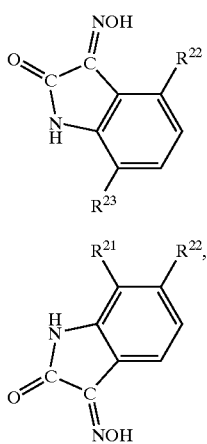

14a

14b which are reacted by heating under reduced pressure in the presence of inert solvents whose boiling points are not below the boiling point of the resulting cleavage products, e.g. diethyl glycol ether, diethylene glycol dimethyl ether, tetraethylurea, tetrabutylurea, dimethylethyleneurea, dimethylpropyleneurea, diethyl phthalate, diethylhexyl phthalate, octaethylene glycol or nonaethylene glycol, to give the corresponding o-aminobenzo-nitriles of the formula 15a or 15b

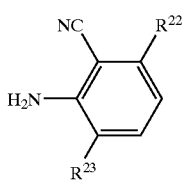

15a

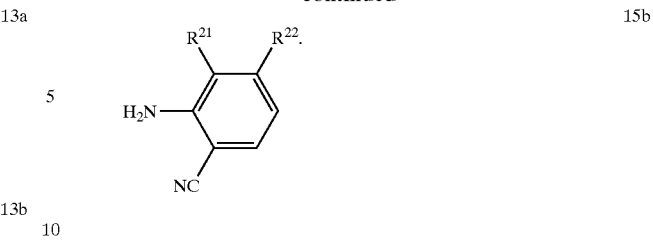

15b

According to a further process, the isatins of the formula 10a or 10b can also be reacted with aqueous hydrogen peroxide in an aliphatic carboxylic acid, such as glacial acetic acid, in the presence of conc. sulfuric acid to give the isatoic anhydrides of the formulae 16a and 16b

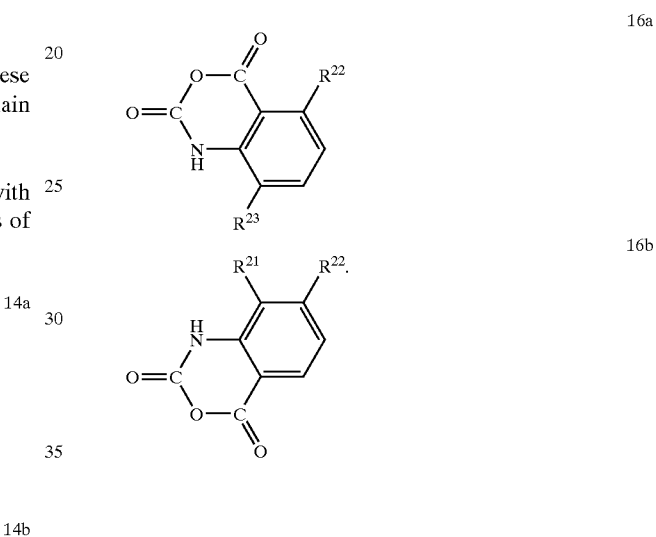

16a

16b

The latter can be converted into the anthranilic esters of the formulae 13a and 13b analogously to the corresponding reaction of the isatins 10a and 10b with $C_1$–$C_3$-alkanols in the presence of a base.

If the nucleophile used is ammonia in aqueous solution, instead of this the carbamoyl derivatives 17a and 17b are obtained.

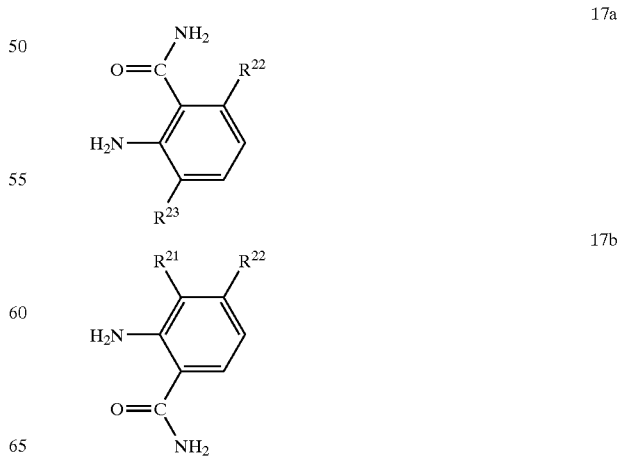

17a

17b

These can be converted—expediently after conversion in corresponding mineral acid salts—by dehydrating agents, e.g. phosphorus oxychloride, into the corresponding nitrites of the formulae 15a and 15b

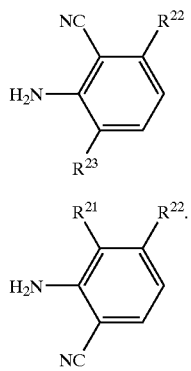

15a

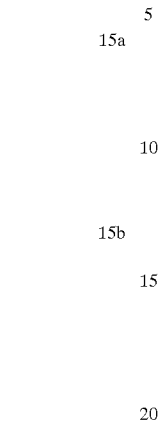

15b

For the preparation of the compounds 1az, in which $R^{21}$ is a methoximinomethyl radical, the reaction described in scheme 1 below, by way of example, is available, where, starting from a substituted o-nitrobenzaldehyde 2z, the oxime ether 6z is obtained by reacting with hydroxylamine hydrochloride in the presence of a base and subsequent methylation, e.g. using methyl iodide. This can also be obtained by direct reaction with methyl hydroxylamine hydrochloride 7 in the presence of a base and then reduced to the aniline derivative 1az, e.g. by reduction with iron.

Scheme 1

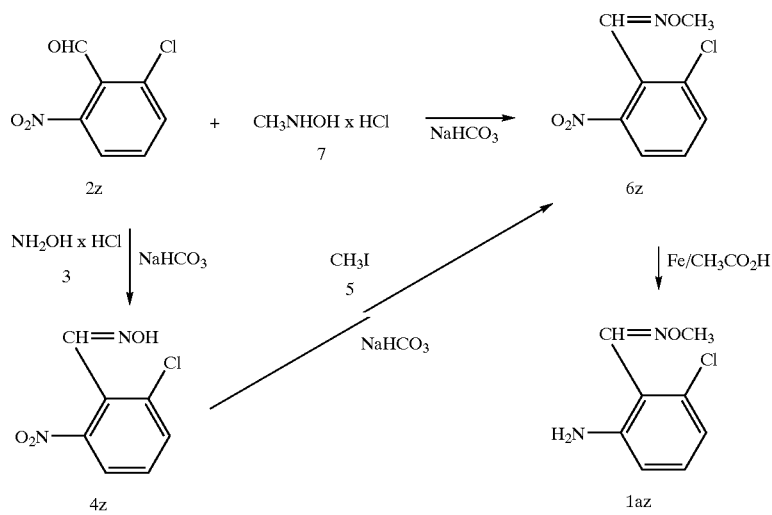

Methods for the preparation of oxime ethers are described in Synthesis 1984, 266, Chem. Ber. 83, 78 (1950) and 34, 1330 (1901).

For the preparation of the isatins needed as further starting materials, e.g. of the isatins 10az and 10bz, substituted anilines 8az and 8bz are reacted with chloral hydrate and hydroxylamine to give the corresponding isonitrosoacetanilides 9az and 9bz and these are cyclized with sulfuric acid according to scheme 2 below. The synthesis of isatins is described, for example, in Beilstein, 21, I 402–405 and 21, IV 5451.

Scheme 2

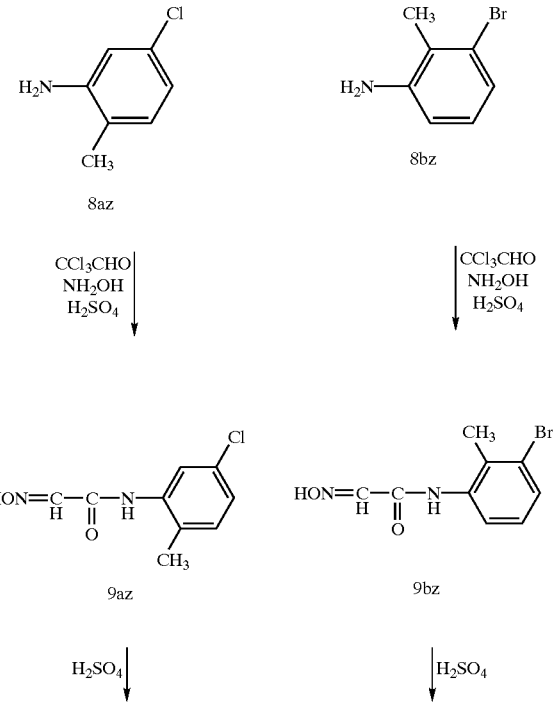

-continued

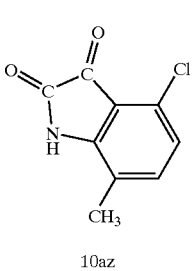

10az

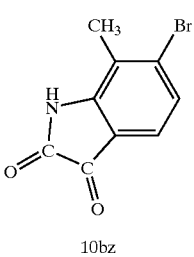

10bz

The isatins 10az and 10bz can be converted into methyl anthranilates 13az and 13bz according to scheme 3, for example by reaction with methanol in the presence of sodium methoxide and aqueous hydrogen peroxide. The process is described in EP 32672 A. The isatins 10az and 10bz can furthermore also be converted into their β-oximes according to JP-A-62234080 and these can be converted into substituted o-aminobenzonitriles 15az and 15bz by heating under reduced pressure according to the processes of DE 1231 709, see also scheme 3.

According to an alternative process, according to Angew. Chem. 1980, 92, 196, the isatins 10az and 10bz can, however, also first be reacted with aqueous hydrogen peroxide in an aliphatic carboxylic acid, such as glacial acetic acid, in the presence of conc. sulfuric acid to give the isatoic anhydrides 16az and 16bz according to scheme 4. The latter, on reacting with alcohols in the presence of a base, for example triethylamine, afford the anthranilic esters 13az and 13bz. On reaction with aqueous ammonia, the carbamoyl derivatives 17az and 17bz are obtained according to scheme 4. These can expediently be converted into the corresponding nitriles 15az or 15bz in the form of their salts—for example as hydrochlorides—using dehydrating agents, such as phosphorus oxychloride.

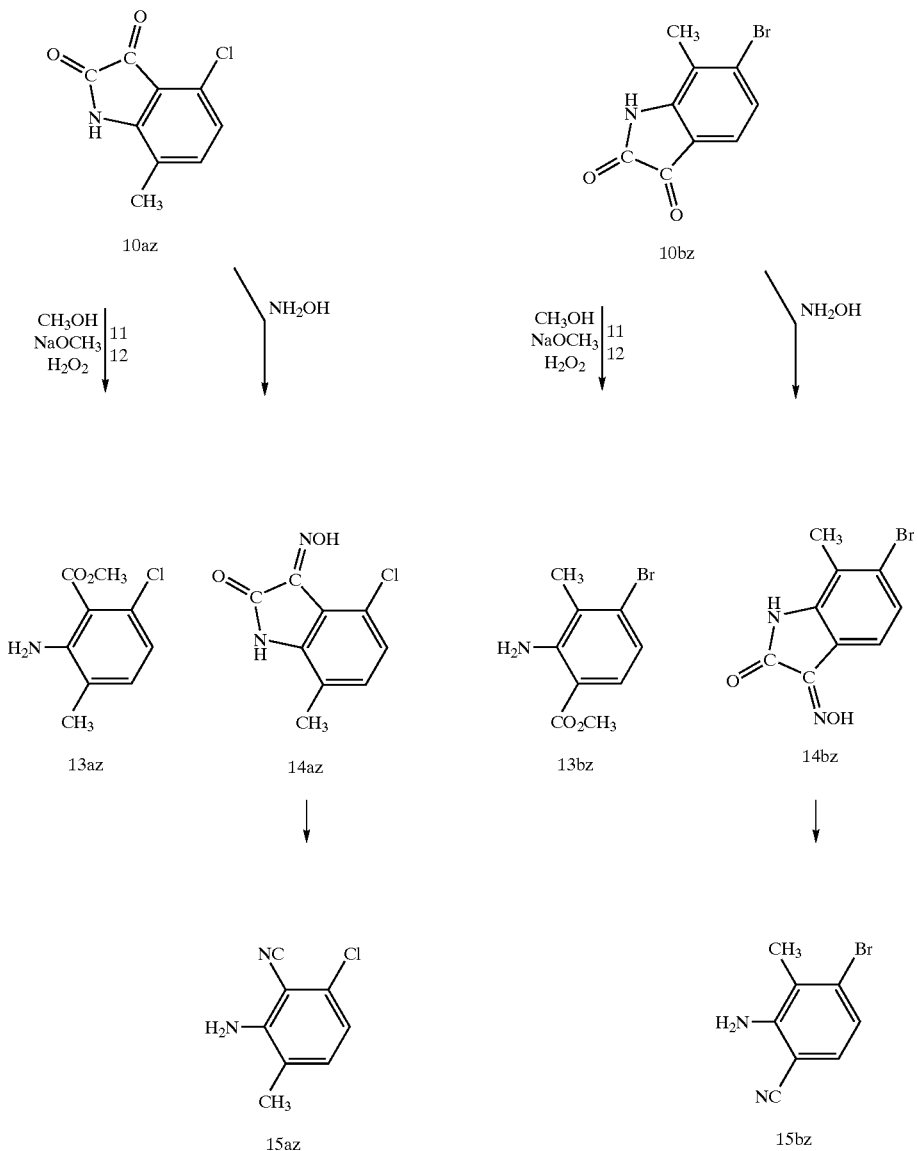

Scheme 3

Scheme 4

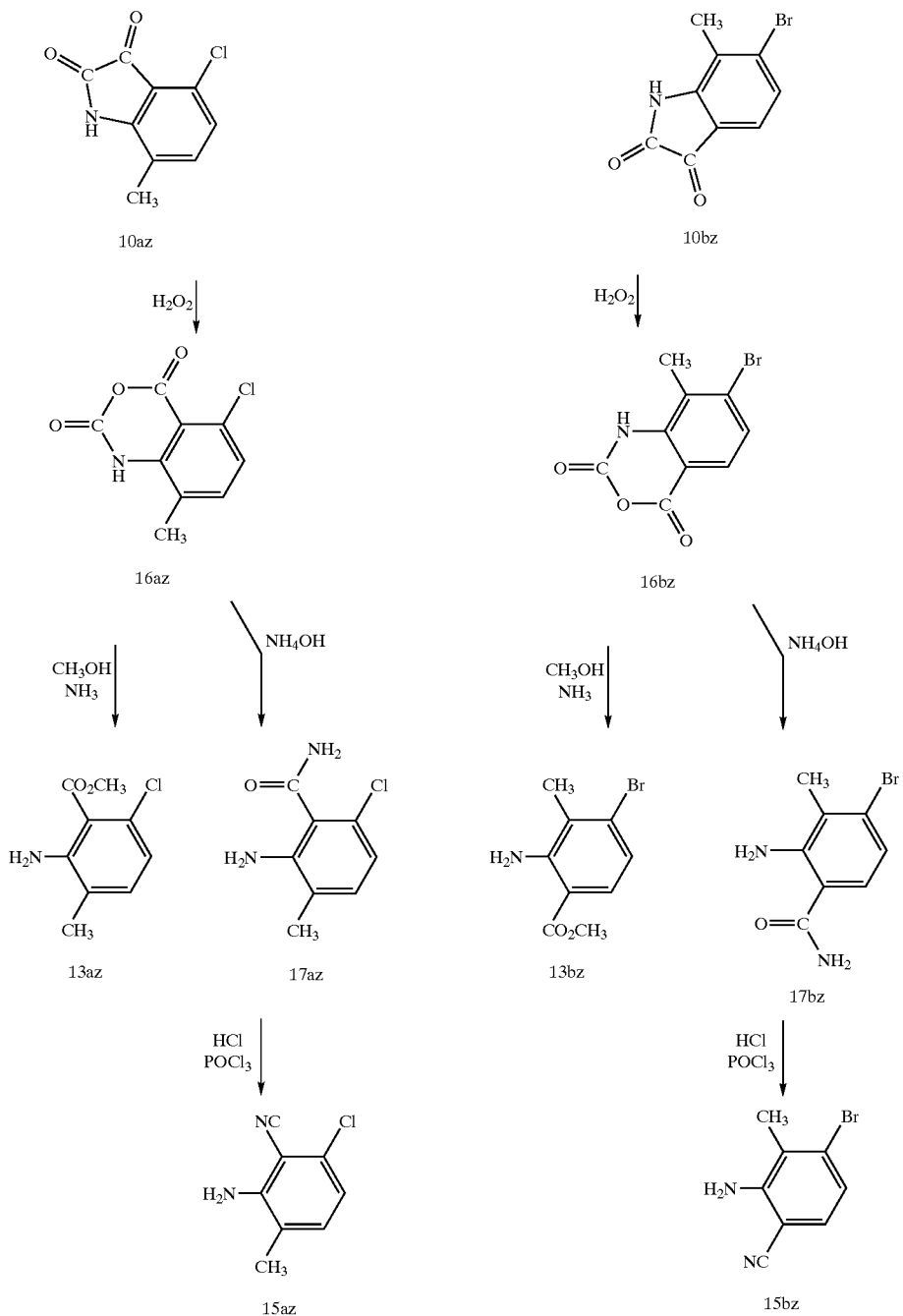

The ring opening of isatoic anhydrides with alcohols is described in J. Med. Chem. 1988, 31, 2136 and WO 97/08130. If aqueous ammonia is used as a nucleophile for the ring opening, the reaction can be carried out according to the procedure of DE 15 43 332. The dehydration of the carbamoyl derivatives to corresponding benzonitriles can be carried out according to the procedures of J. Chem. Soc. Chem. Commun. 1994, (15), 1767 and J. Heterocycl. Chem. 1997, 34, 1661.

3-Chloro-2-methoxymethylaniline is disclosed in EP 127 114 and DE 23 45 443; it can also be converted into corresponding 6-substituted carboxylic acid derivatives according to schemes 2–4.

In addition, however, anthranilic esters of the formula 13a or 13b

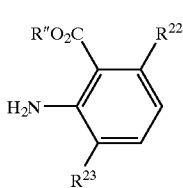

13a

-continued

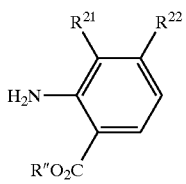
13b in which R'', for example, is a $C_1$–$C_3$-alkyl radical and $R^{21}$, $R^{22}$ and $R^{23}$ are Cl, Br, $C_2$–$C_3$-alkyl, $R^{21}$ and $R^{23}$ are further CN or $C_1$–$C_3$-alkoxycarbonyl or $R^{23}$ is further $C_1$–$C_3$-alkoxy, can be reacted, for example after protection of the amino group, with an acylating agent 18

R'C(O)G      18 in which R' is a $C_1$–$C_4$-alkyl radical and G is a nucleophilically displaceable leaving group (examples have already been mentioned above) to give the acylanilines 19a or 19b

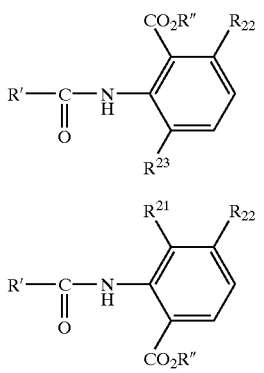
19a

19b these can be reduced using a complex metal hydride 20

Me$^I$Me$^{III}$H$_4$      20 in which Me$^I$ or Me$^{III}$ in each case are metals of the 1st or 3rd main group, to give the benzyl alcohols 21a or 21b

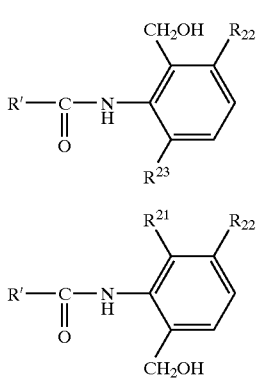
21a

21b these can be reacted with an alkylating agent RG (R=$C_1$–$C_3$-alkyl) in the presence of a base to give the alkoxymethyl representatives 22a or 22b

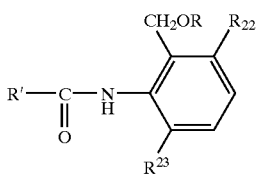
22a

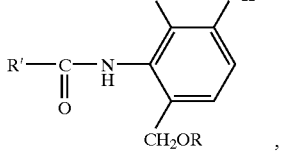
22b and the latter can be reacted in the presence of aqueous alkali or mineral acid with removal of the protective group to give the free anilines 23a or 23b.

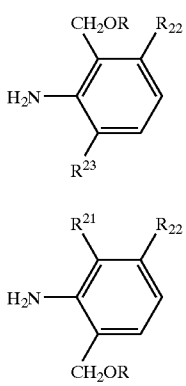
23a

23b

Instead of the anthranilic esters 13a or 13b, the corresponding anthranilic acids can also be used for the reduction.

In the case of the use of the anilines 13az or 13bz, in which $R^{23}$ or $R^{21}$ and R'' are methyl and $R^{22}$ is Cl, the preparation, for example, of methoxymethyl representatives 23az or 23bz is carried out according to scheme 5:

Scheme 5

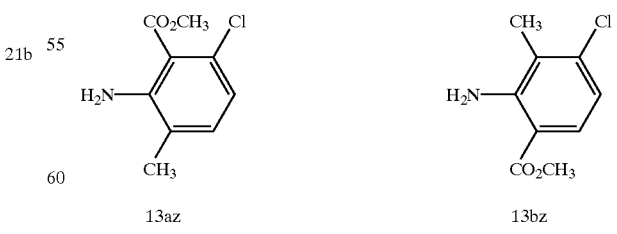

13az      13bz

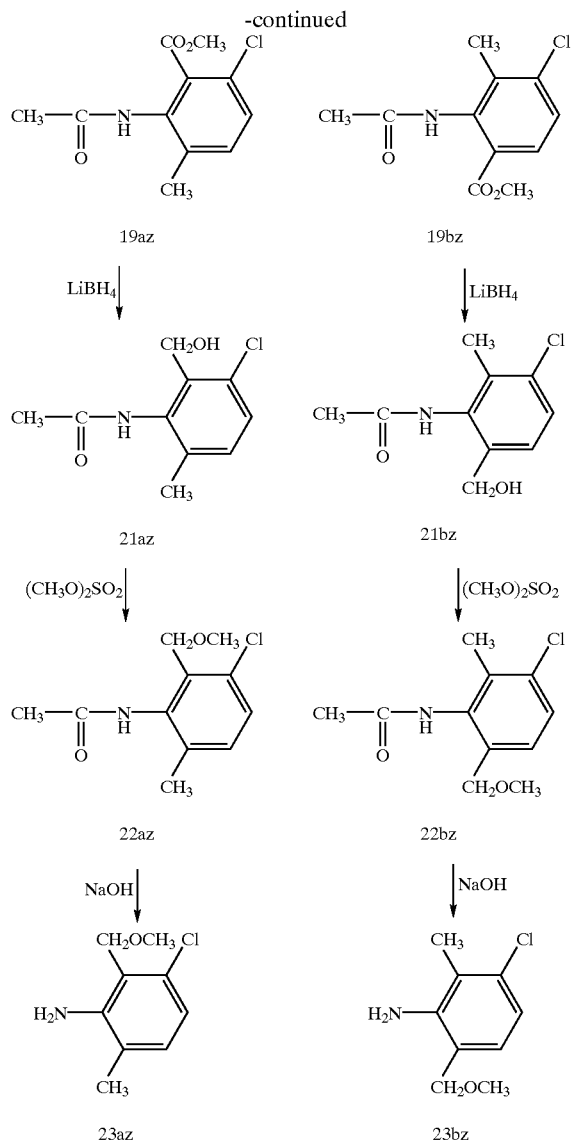

However, it is also possible to halogenate the acylanilines of the formula 19c or 19d

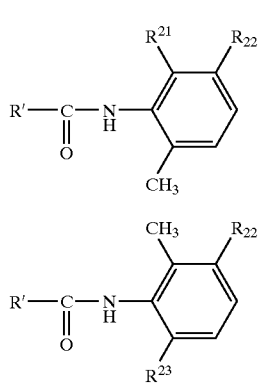

in which $R^{21}$ and $R^{23}$ are Cl, Br, CN or $C_1$–$C_3$-alkoxycarbonyl and $R^{22}$ is Cl or Br, on the tolyl side chain to give the benzyl halides 24c or 24d, in which Hal is Cl or Br,

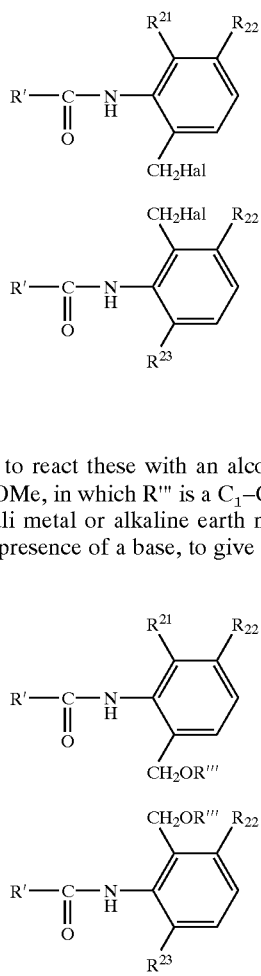

and to react these with an alcohol R'''OH or an alcoholate R'''OMe, in which R''' is a $C_1$–$C_3$-alkyl radical and Me is an alkali metal or alkaline earth metal atom, if appropriate in the presence of a base, to give the benzyl ethers 22c or 22d

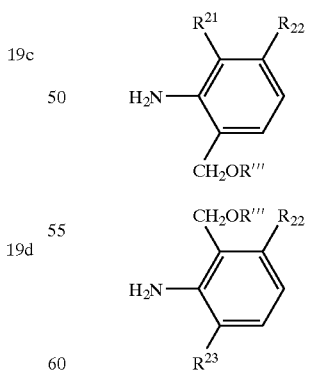

and to cleave these in the presence of aqueous alkali or dilute sulfuric, hydrochloric or phosphoric acid to give the free anilines 23c or 23d.

In the case of the use of the acylanilines 19cz or 19dz, in which $R^{21}$ and $R^{23}$ are CN and $R^{22}$ is Cl, the preparation, for example of the methoxymethyl representatives 23cz or 23dz, is carried out according to scheme 6:

Scheme 6

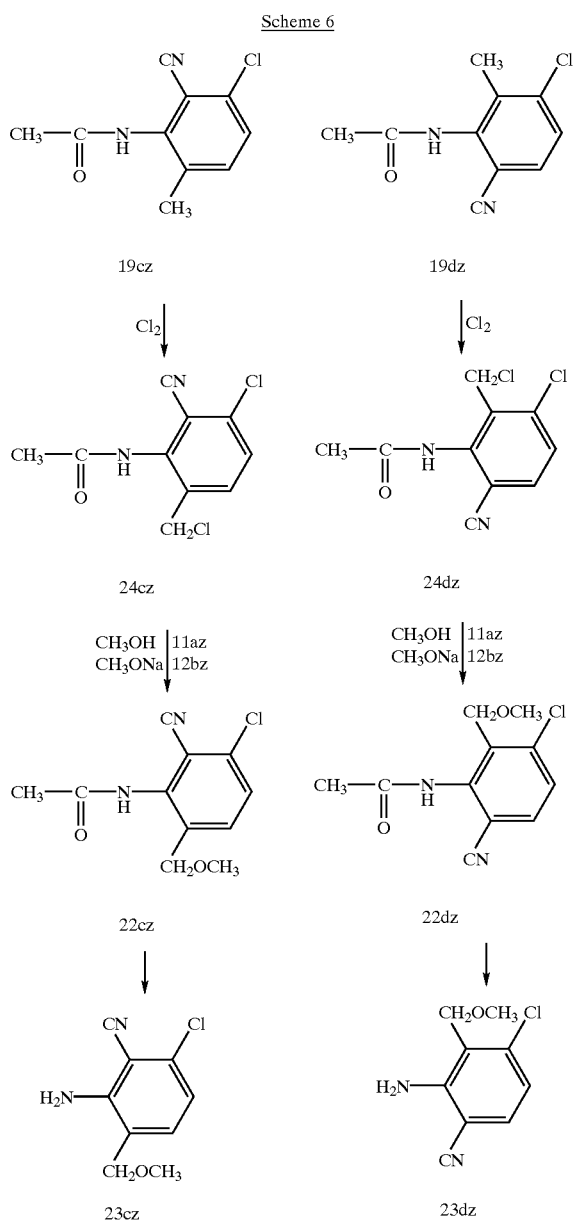

If, instead of the nitrites 19cz or 19dz, corresponding anthranilic esters are used, these are as a rule also hydrolyzed on removal of the acylamino group, so that they subsequently have to be esterified again, for example by boiling under reflux in alcoholic hydrochloric acid while passing through hydrogen chloride gas.

The reaction steps of scheme 1 are illustrated in greater detail below. By addition of an alkali metal or alkaline earth metal hydrogen carbonate to the aqueous solution of an o-alkylhydroxylamine hydrochloride with stirring at 10 to 30° C. during 5 to 30 min, the alkylhydroxylamine is released as the base.

Sodium, potassium, magnesium or calcium hydrogen carbonate is suitable as the alkali metal or alkaline earth metal hydrogen carbonate.

The free hydroxylamine is added as an aqueous solution with stirring at 40 to 70° C., preferably 50 to 60° C., within 10 to 30 min to the solution of the nitrobenzaldehyde in an inert organic solvent, and the mixture is stirred for 1 to 4, preferably 2 to 3, h at 50° C.

The molar ratio of starting substance 2 to 7 is in general 0.9 to 1.2, preferably 0.95 to 1.1.

Instead of the O-alkylhydroxylamine hydrochloride, it is also possible to convert hydroxylamine hydrochloride into the free base in an analogous manner and to react it as described with the aldehyde derivative 2. The oxime 4 obtained in this way must then additionally be alkylated using an alkylating agent 5.

Suitable alkylating agents 5 are alkyl halides, e.g. alkyl chlorides, bromides or iodides, dialkyl sulfates or arylsulfonic acid esters. Expediently, the alkylating agent is allowed to act on the oxime 5 at 10 to 60° C., preferably 20 to 40° C., for 0.5 to 5 h, in particular 1 to 2 h, in the presence of a base.

Bases used can be the abovementioned hydrogen carbonates, furthermore alkali metal or alkaline earth metal carbonates and also alkali metal and alkaline earth metal hydroxides. Alkali metal is preferably sodium or potassium, alkaline earth metal magnesium or calcium.

The molar ratio of 4 to 5 is in general 0.9 to 1.4, preferably 1.1 to 1.2.

Analogous alkylations are described in Houben-Weyl, Methoden der Organischen Chemie [Methods of Organic Chemistry], IVth edition, volume VI/3, pp. 24–37.

The oxime ethers 6 thus obtained are then reduced using iron in the presence of an acid. Advantageously; the oxime ether 6 is brought into contact in a mixture of a carboxylic acid, such as acetic acid, and an alcohol, such as methanol, with a mixture of iron powder in the same mixture of carboxylic acid and alcohol for 2 to 6 h, advantageously 3 to 4 h, at 70 to 80° C.

The reduction of the oxime ether 6, however, can also be carried out using hydrogen in the presence of a metal catalyst at 10 to 40° C. The reduction can also be carried out under pressure in an autoclave, for example using Raney nickel. Expediently, hydrogenation is carried out at 20 to 80° C., advantageously 40 to 60° C., and a hydrogen pressure of 1 to 50 bar, advantageously 10 to 20 bar.

Suitable metal catalysts are platinum, palladium, Raney nickel, Raney cobalt or alternatively platinum oxide. Suitable hydrogenation processes are described in Houben-Weyl, Methoden der Organischen Chemie [Methods of Organic Chemistry], IVth edition, volume 11/1, pp. 341–359.

In the reaction steps shown in scheme 2, the aniline 8 is expediently introduced in water, and, successively, hydroxylammonium sulfate is first added in portions, then conc. sulfuric acid dropwise and finally choral with stirring at 20 to 40° C. The mixture is warmed to 50° C. for 10 to 30 min and a pH of 1.5–2 is then set by addition of conc. sodium hydroxide solution. After 6 to 16 h, advantageously 8 to 12 h, at room temperature, the precipitate formed is isolated, taken up in a base, washed with a water-immiscible organic solvent, and the isonitrosoacetanilide 9 is precipitated by addition of an acid, e.g. sulfuric acid.

In general, 0.9 to 1.2, preferably 0.95 to 1.05, mol of choral and 2 to 4 mol, preferably 2 to 3 mol, of hydroxylammonium sulfate are used per mole of 7.

For the cyclization of the isonitrosoacetanilides 9 to the corresponding isatins 10, the starting substances 9 are treated for 2 to 5 h at 60 to 90° C., advantageously 70 to 80° C., with a strong acid, e.g. 90% strength sulfuric acid.

The synthesis of the starting substances 9 and 10 in this context follows the preparation methods described in Beilstein, volume 21, 402–405.

In the reaction steps shown in scheme 3, the isatins 10 are oxidized with hydrogen peroxide in the presence of alcohols 11 and alkali metal alkoxides 12 to give the anthranilic esters 13. To this end, aqueous hydrogen peroxide is added to the starting substances 10 in a mixture of an alcohol 9 and its alkali metal alkoxide with cooling, and the mixture is treated at room temperature for 20 to 60 min, expediently 30 to 40 min.

The molar amounts in which the starting substances are reacted are 40 to 100, in particular 60 to 80, mol of alcohol, 1 to 5 mol, in particular 1 to 3 mol, of alkali metal alkoxide and 1 to 3, in particular 1 to 1.5, mol of hydrogen peroxide per mole of isatin 10.

The preparation of the anthranilic esters 13 in this case follows the process described in EP 32 672.

The isatins 10 can furthermore be converted into their β-oximes according to the manner described in scheme 1, furthermore also according to J. Heterocycl. Chem. 1980, 17, 65.

If these are heated in the presence of inert solvents or diluents whose boiling points are not below the boiling point of the resulting o-aminobenzonitriles 15, to 200 to 400° C., preferably 200 to 300° C., at 0.1 to 200 mbar, preferably 10 to 120 mbar, the compounds 15 distil over in high purity. Suitable inert solvents and diluents have already been mentioned above. The preparation follows the procedure described in DE 12 31 709.

In the reaction steps shown in scheme 4, the isotins 10 are oxidized with hydrogen peroxide in a carboxylic acid, such as acetic acid, as the reaction medium in the presence of catalytic amounts of sulfuric acid firstly to the isatoic anhydrides 16. For this, the isatins 10 are treated in acetic acid with (per mole of isatin 10) 4–8 ml, preferably 5–6 ml, of conc. sulfuric acid and hydrogen peroxide, and the reaction temperature is kept at 50–80° C., preferably 60–70° C. The molar amounts of hydrogen peroxide per mole of isatin 10 are 0.95 to 1.3, preferably 1.0 to 1.15, mol.

The preparation follows the reaction procedure described in Angew. Chem. 1980, 92, 196.

For the conversion of the isatoic anhydrides 16 into the anthranilic esters 13, the starting substances 16 are suspended in excess alcohol as the reaction medium, 0.6 to 1 mol, preferably 0.7 to 0.9 mol, of an organic base, such as triethylamine, tri-n-propylamine, cyclohexyldimethylamine or N-methylmorpholine, is added per mole of starting substance, and the mixture is treated for 1 to 5 h, preferably 2 to 3 h, at 50 to 80° C., preferably 60 to 70° C. The anthranilic esters 13 are prepared in the customary manner. Instead of the abovementioned organic bases, it is also possible to use 1 to 10, preferably 2 to 5, mol % of a highly nucleophilic organic base, such as 4-dimethylaminopyridine, as a catalyst.

The working procedure follows the procedure described in WO 97/08130 and J. Med. Chem. 1988, 31, 2136.

Instead of with alcohols, the ring opening of the isatoic anhydrides 16 can also be carried out using ammonia to give the anthranilamides 17. For this, aqueous ammonia and compound 16 are brought into contact in a polar aqueous solvent, such as dimethylformamide, dimethylacetamide or N-methylpyrrolidone, at 70 to 95° C., advantageously 80 to 90°. The amount of ammonia, based on the starting substance 16, is 0.95 to 1.3, preferably 1.1 to 1.2, mol.

The working procedure follows the procedure described in DOS 1543 332.

For the conversion of the anthranilamides 17 into the corresponding benzonitriles 15, the starting substances 17 are expediently treated in the form of the hydrochloride with dehydrating agents, such as phosphorus oxychloride, for 1 to 8 h, advantageously 3 to 4 h, at 110 to 150° C., preferably 120 to 130° C. The process follows the procedures described in J. Chem. Soc. Chem. Comm., 1994, (15), 1767, J. Heterocycl. Chem. 1997, 34, 1661.

Surprisingly, it has been found that the preparation of the compounds according to the invention, in which at least one of the radicals $R^{21}$ and $R^{23}$ is CN, takes place smoothly and in high yield by treatment of the corresponding carbamoyl compounds, i.e. compounds of the formula 1 in which at least one of the radicals $R^{21}$ and $R^{23}$ is $CONH_2$, with phosphorus oxychloride. With respect to the prior art, e.g. Houben-Weyl, Methoden der Organischen Chemie [Methods of organic Chemistry], 4th edition, volume 12/2, pages 387 and 448 and volume E2, p. 527, the formation of phosphoric acid anilide derivatives would have been expected. The starting compounds are expediently employed here in the form of a salt with an inorganic or organic acid. Suitable acids are, for example, hydrochloric acid, hydrobromic acid, sulfuric acid, phosphoric acid, nitric acid, acetic acid or propionic acid. Hydrochloric acid is preferred.

The phosphorus oxychloride is in general used in an excess. The reaction conditions are specified above in connection with the benzonitriles 15.

In the reaction steps shown in scheme 5, the anthranilic esters 13 are protected with an acyl radical. Suitable acylating agents are chlorides or bromides of acetic acid, propionic acid, butyric acid, isobutyric acid or valeric acid, further more anhydrides of these acids. It is also possible to employ mixed anhydrides, for example formyl acetate. Expediently, the acylating agent, when using an anhydride at 20 to 140° C., advantageously 80 to 120° C., is allowed to act on the anthranilic ester in an inert solvent in the course of 4 to 20 h, advantageously 6 to 12 h. When using acid chlorides as acylating agents, the acid chloride is contacted with the mixture of the anthranilic ester 13 and a base in an inert solvent at 10 to 60° C., advantageously 20 to 30° C., for 2 to 20 h, advantageously 6 to 12 h. It is possible to use as base the abovementioned organic and inorganic bases, furthermore pyridine, α-, β- or γ-picoline, lutidine, quinoline or acridine. When using acid chlorides or bromides, it is also possible to work in a two-phase system which is formed when using water. When using anhydrides as acylating reagent, the acylation can be catalytically accelerated by highly nucleophilic bases, such as p-dimethylaminopyridine or p-pyrrolidinopyridine. The molar ratios in which the starting substances are reacted with one another are 0.95 to 1.3, advantageously 1.0 to 1.1, mol of acylating agent and base per mole of anthranilic ester 13. The catalyst is expediently employed in an amount from 0.5 to 1.0, advantageously 1 to 3, mol % per mole of anthranilic ester 13.

For the reduction of the acylated anthranilic ester 19, this is brought into contact in an inert solvent with a complex metal hydride, such as sodium borohydride, in one of the abovementioned solvents at 10 to 65° C., advantageously 20 to 50° C., for 2 to 10 h, advantageously 3 to 6 h. Suitable inert solvents are acetonitrile or aqueous alcohols (when using sodium borohydride) or diisopropyl ether or tetrahydrofuran (when using lithium aluminum hydride or lithium borohydride).

The molar ratios in which the starting substances are reacted with one another are 0.5 to 3, advantageously 0.75 to 2.5, mol of lithium borohydride per mole of starting substance 20.

The starting substances 19 can also be hydrolyzed at the ester group by treatment with 0.95 to 1.1 mol, advantageously 1.0 to 1.03 mol, of aqueous alkali at 10 to 80° C., advantageously 20 to 60° C., for 1 to 10 h, advantageously 2 to 6 h, and then reduced with a complex metal hydride as above. The process follows the procedure described in Organikum, VEB Deutscher Verlag der Wissenschaften, Berlin 1976, 15th edition, pp. 612–616.

The benzyl alcohols 21 are then alkylated by treatment with an alkylating agent 5. The reaction is carried out under the same reaction conditions as for the alkylation of the oxime 4 as in scheme 1.

For the release of the o-alkoxymethylaniline 23, compound 22 is hydrolyzed for 1 to 12 h at 20 to 120° C., advantageously 2 to 8 h at 60 to 100° C., with aqueous alkali, expediently 0.95 to 1.2 mol, advantageously 1.0 to 1.1 mol.

In the reaction steps shown in scheme 6, the protected anilines 19 are subjected to a chlorination on their tolyl side chain. For this, elemental chlorine and an apparatus for continuous chlorination, such as for the chlorination of toluene to benzyl chloride described in Houben-Weyl, Methoden der Organischen Chemie [Methods of Organic Chemistry], 4th edition, volume 5/3, p. 520, can be used. However, it is also possible to use N-chloro or N-bromo compounds with positively induced halogen, such as described ibid. p. 800. For example, on pp. 800–801, the chlorination of toluene with N-chlorosuccinimide under exposure to light or with addition of peroxides for side-chain chlorination is described in greater detail.

Ibid., p. 807 illustrates the chlorination of the tolyl side chain using 1,3-dichloro-5,5-dimethylhydantoin. Instead of elemental halogen, it is also possible to use the milder acting sulfuryl chloride and to catalyze the reaction by addition of a free radical initiator, such as azoisobutyronitrile or benzoyl peroxide. The reaction follows the procedure described in Houben-Weyl, volume V/3, p. 892.

Suitable solvents are relatively highly chlorinated hydrocarbons such as dichloro- and trichlorobenzene, chloroform, in particular carbon tetrachloride, furthermore acetonitrile or acetic acid. However, it is also possible to work without solvent and to pass chlorine or sulfuryl chloride directly into a melt of the starting substance 20.

The amount of chlorinating reagent is 0.7 to 1.5, expediently 0.95 to 1.1, mol of chlorinating reagent per mole of starting substance 20. Depending on the chlorinating reagent, the reaction is carried out at 10 to 200° C., advantageously 20 to 150° C., for 10 min to 10 h, advantageously 0.5 to 6 h.

For the conversion of the benzyl chlorides 24 into their alkoxymethyl ethers an alkanol 11 and expediently its alkoxide 12 are brought into contact with 14 at 10 to 100° C., advantageously 20 to 80° C., for 0.5 to 8 h, advantageously 1 to 4 h. Instead of the alkoxide 12, it is also possible to employ one of the abovementioned bases or an alkali metal hydroxide in the alcohol concerned.

The molar amounts in which the alkoxide 12 or the base is employed are 0.95 to 1.2, advantageously 1.0 to 1.1, mol per mole of benzyl chloride 24.

The process is described in Houben-weyl, 4th edition, volume 6/3, pp. 24–32.

For the release of the compounds 23, the starting substances 22 are treated with aqueous alkali (expediently 0.95 to 1.2 mol, advantageously 1.0 to 1.1 mol) for 1 to 20 h, advantageously 2 to 10 h, at 20 to 120° C., advantageously 70 to 100° C.

All reaction steps described above can be carried out continuously or batchwise, without pressure or under pressure.

The concentration of the starting materials in the solvent is 0.1 to 5 mol/l, preferably 0.2 to 2 mol/l.

As a rule, the reaction mixtures are worked up by methods known per se, for example by dilution of the reaction solution with water and subsequent isolation of the product by means of filtration, crystallization or solvent extraction, or by removal of the solvent and distillation or distribution of the residue in a mixture of water and a suitable organic solvent and working-up of the organic phase to the product.

If not stated otherwise, the solvents used for the above reactions—depending on the temperature range—are hydrocarbons such as pentane, hexane, cyclopentane, cyclohexane, toluene, xylene, chlorinated hydrocarbons such as methylene chloride, chloroform, 1,2-dichloroethane, 1,1,2,2-tetrachloroethane, chlorobenzene, 1,2-, 1,3- or 1,4-dichlorobenzene, ethers such as 1,4-dioxane, tetrahydrofuran, anisole, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as dimethylformamide, N-methylpyrrolidone, nitro hydrocarbons such as nitrobenzene, ureas such as tetraethylurea, tetrabutylurea, dimethylethyleneurea, dimethylpropyleneurea, sulfoxides such as dimethyl sulfoxide, sulfones such as dimethyl sulfone, diethyl sulfone, tetramethylene sulfone, nitriles such as acetonitrile, propionitrile, butyronitrile or isobutyronitrile; water or alternatively mixtures of individual solvents.

The aniline compounds are accessible in good yields. They can also be prepared on a relatively large scale. To a particular extent, they are therefore suitable as starting materials for the preparation of compounds of the general formula A

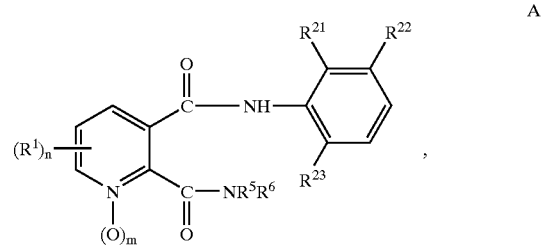

in which $R^1$, $R^5$, $R^6$, $R^{21}$, $R^{22}$, $R^{23}$, m and n have the meanings indicated above.

The further processing of the aniline compounds to the compounds of the formula A can be carried out by literature processes known per se, e.g. analogously to the synthesis routes described in EP 799 825. The contents of EP 799 825 are part of the present disclosure.

The preferred further processing process comprises the reaction of a pyridine-2,3-dicarboxylic anhydride compound of the formula B

with an aniline of the formula 1. The reaction leads to a compound of the formula C or D

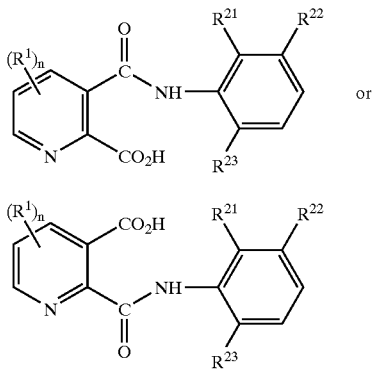

or a mixture thereof. It is in general carried out in an inert solvent, e.g. a chlorinated solvent, such as dichloromethane or 1,2-dichloroethane, an aromatic hydrocarbon, such as toluene or xylene, or an ether, such as diethyl ether, dioxane or tetrahydrofuran. The reaction can be carried out in a wide temperature range, e.g. from room temperature up to the boiling point of the solvent.

The reaction product is cyclized using a dehydrating agent, such as acetic anhydride or thionyl chloride, with or without inert solvent, to give an imide of the formula E

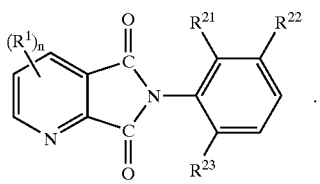

Possible inert solvents are the solvents indicated above. Alternatively, the cyclization can be carried out by heating (1 to 20 h) of the compounds C and/or D as a melt, preferably at a temperature in the range from 150° C. to 250° C.

The imide is then reacted with an amine of the formula $HNR^5R^6$ to give the corresponding compound of the formula A ($R^1$, $R^5$, $R^6$ and n have the meanings indicated above). The reaction conditions for the above reaction steps are described in detail in EP-A-799 825. If a compound of the formula A where m=1 is desired, an oxidation is carried out at the stage of the imide using a suitable oxidant, such as hydrogen peroxide or organic peracids, e.g. peracetic acid, m-chloroperbenzoic acid, see EP-A-799 825. The pyridine-2,3-dicarboxylic anhydrides can be prepared according to known processes, for example by treatment of the pyridine-2,3-dicarboxylic acids with phosgene in the presence of dimethylformamide according to the process described in U.S. Pat. No. 4,439,607.

Further pyridinedicarboxylic acid starting materials are described in EP 227 932, 322 616, 461 403, 422 456, 661 282 and 663 399 or can be prepared according to the methods described there. The amines of the formulae $Q-NH_2$ and $HNR^5R^6$ are known or can be prepared according to processes known to the person skilled in the art.

The following examples illustrate the invention without restricting it.

EXAMPLE 1

3-Chloro-2-Methoxyiminomethylaniline a) 3-Chloro-2-Methoxyiminomethylanilinonitrobenzene 25.4 g (0.302 mol) of sodium hydrogen carbonate were added in portions at 22° C. with stirring to a mixture of 126 g (0.302 mol) of 20% strength o-methylhydroxylamine hydrochloride in 140 ml of water in the course of 10 min. This solution was then added to 50 g of 2-chloro-6-nitrobenzaldehyde in 270 ml of toluene at 50 to 55° C. with stirring in the course of 30 min and the mixture was stirred at 50° C. for 2 h. After cooling, 250 ml of water and 250 ml of toluene were added to the reaction mixture for the separation of the phases. The aqueous phase was extracted once more with toluene. The organic extracts were washed with water and dilute sodium chloride solution, dried over magnesium sulfate and concentrated in vacuo. 52 g (84% of theory) of the title compound were obtained as a yellowish oil of $n_D^{23}$=1.5691.

b) 3-Chloro-2-Methoxyiminomethylaniline 35.1 g (0.629 mol) of iron powder were introduced in a mixture of 100 ml of acetic acid and 140 ml of methanol and warmed to 70° C. 45 g (0.21 mol) of the compound from 1a) in 100 ml of acetic acid and 140 ml of methanol were then added with stirring at 70 to 75° C. in the course of 45 min and the mixture was stirred at 70° C. for 3 h. After cooling, the suspension was poured onto 3 l of water and stirred with 0.5 l of ethyl acetate. After filtering off with suction, the precipitate was washed with 0.5 l of ethyl acetate and the phases were separated. The aqueous phase was extracted a further 2× with ethyl acetate, and the organic extracts were combined, dried over magnesium sulfate and concentrated in vacuo. 38.7 g (95% of theory) of the title compound were obtained as a yellowish oil of $n_D^{23}$=1.6140.

EXAMPLE 2

Methyl 2-Amino-6-chloro-3-methylbenzoate 110 g (0.52 mol) of 6-chloro-3-methylisatoic anhydride were introduced into a mixture of 750 ml of methanol and 47.6 g (0.47 mol) of triethylamine at 22° C. with stirring and the mixture was then stirred at 65° C. for 2 h. The reaction mixture was concentrated in vacuo, and the residue was taken up in methylene chloride and extracted 3× with 0.5 N sodium hydroxide solution. After drying over magnesium sulfate, filtering through silica gel and concentrating in vacuo, 45.5 g (43.8% of theory) of the title compound were obtained as a colorless oil of $n_D^{23}$=1.5765.

EXAMPLE 3

2-Amino-3-chloro-6-methylbenzamide

A solution of 59 ml (0.78 mol) of 25% strength ammonia solution in 207 ml of water and a mixture of 135.2 g (0.64 mol) of 3-chloro-6-methylisatoic anhydride in 705 ml of DMF were added simultaneously to 150 ml of water via 2 dropping funnels in the course of 30 min with stirring at 85 to 90° C., strong evolution of gas occurring. The mixture was stirred at 90° C. for 2 h and at 22° C. for 10 h. The reaction solution was concentrated in vacuo, and the residue was stirred with methyl tert-butyl ether, filtered off with suction and dried. 67.4 g (57% of theory) of the title compound were obtained as a yellowish powder of m.p. 124–128° C.

EXAMPLE 4

2-Amino-3-chloro-6-methylbenzonitrile 1.18 g (0.033 mol) of hydrogen chloride, dissolved in 35 ml of diethyl ether, were added at 22 to 30° C. with stirring to a suspension of 5 g (0.027 mol) of the compound from example 3 in 50 ml of 1,2-dichloroethane and the mixture was then concentrated in vacuo. The residue was treated with 150 ml of phosphorus oxychloride and the mixture was stirred at 120° C. for 3 h. The reaction mixture was then concentrated in vacuo, the residue was dissolved in methylene chloride, and the solution was treated with water and neutralized using 2 N sodium hydroxide solution. After the phase separation, the organic phase was again washed with water, then with saturated sodium chloride solution, and dried over magnesium sulfate. After concentration, 2.4 g (48% of theory) of the title compound were obtained as a yellowish powder of m.p. 77–80° C.

EXAMPLE 5

2-Amino-4-chloro-3-methylbenzamide

A suspension of 4.64 g (0.0219 mol) of 3-methyl-4-chloroisatoic anhydride in 21 ml of DMF and 3.1 g (0.0219 mol) of 25% strength ammonia water in 6 ml of water were allowed to run simultaneously at 80° C., over 2 additions, into 8 ml of water with stirring in the course of 15 min. After stirring at 80° C. for 1 h, the mixture was cooled and extracted 2× with ethyl acetate. The organic phase was dried over magnesium sulfate and concentrated in vacuo, 2.61 g (64.4% of theory) of the title compound being obtained as colorless crystals of m.p. 206–208° C.

EXAMPLE 6

2-Amino-4-chloro-3-methylbenzonitrile

According to the procedure of example 4, in the reaction of 5 g (27.1 mmol) of the compound from example 5, 1.18 g (32.5 mmol) of hydrogen chloride in 100 ml of 1,2-dichloroethane, then 150 ml of phosphorus oxychloride, 2.39 g (52.9% of theory) of the title compound were obtained as a yellowish powder of m.p. 98–99° C.

EXAMPLE 7

2-Amino-6-chloro-3-methylbenzamide

According to the procedure of example 3, in the reaction of 98.8 g (0.467 mol) of 6-chloro-3-methylisatoic anhydride in 330 ml of DMF with 42 ml (0.560 mol) of 25% strength aqueous ammonia solution in 140 ml of water and a further 110 ml of water, 24 g (37% of theory) of the title compound were obtained as a yellowish powder of m.p. 149–152° C.

EXAMPLE 8

2-Amino-6-chloro-3-methylbenzonitrile

According to the procedure of example 4, in the reaction of 2.85 g (0.0154 mol) of the compound from example 7, 0.68 g (0.0185 mol) of hydrogen chloride in 50 ml of 1,2-dichloroethane, then 100 ml of phosphorus oxychloride, 1.3 g (47.5% of theory) of the title compound were obtained as a yellowish powder of m.p. 95–98° C.

EXAMPLE 9

N-(2-Carbamoyl-5-chloro-6-methylphenyl)-3-carboxy-6-methyl-pyridine-2-carboxamide (A) and N-(2-cyano-5-chloro-6-methylphenyl)-6-methylpyridine-2,3-dicarboximide (B)

2.6 g (0.0141 mmol) of the compound from example 5 were added to a mixture of 2.3 g (0.0141 mol) of 6-methylpyridine-2,3-dicarboxylic anhydride and 150 ml of 1,2-dichloroethane, and the mixture was stirred at 83° C. for 15 h. 1.76 g (0.0148 mol) of thionyl chloride were then added and the mixture was stirred at 83° C. for 16 h. 200 ml of methylene chloride and 150 ml of water were added to the reaction mixture and the phases were separated. The insoluble residue was filtered off with suction and dried, 0.91 g (18.5% of theory) of the title compound A being obtained as a yellowish powder of m.p. 252° C. dec.

The organic phase was dried and chromatographed on silica gel, 1.45 g (33% of theory) of the title compound B being obtained as a tacky powder.

$^1$H-NMR (270 MHz, $d_6$-DMSO): δ 8.44 (d/1H), 7.9 (d/1H) Pyr; 8.0 (d/1H), 7.8 (d/1H) Ph; 2.3 (s/3H) $CH_3$.

EXAMPLE 10

3-(2-Cyano-5-chloro-6-methylphenyl)aminocarbonyl-6-methyl-pyridine-2-carboxylic acid N-n-propylamide 0.28 g (4.8 mmol) of n-propylamine was added to a mixture of 0.5 g (1.604 mmol) of the compound B from example 9 and 20 ml of THF and the mixture was stirred at 22° C. for 14 h. The reaction mixture was concentrated in vacuo, stirred in methylene chloride and washed 2× with 0.5 N sodium hydroxide solution. The organic phase was dried and concentrated, 0.2 g (30.3% of theory) of the title compound being obtained as a yellowish powder of m.p. 175–176° C.

EXAMPLE 11

N-(6-Chloro-2-cyano-3-methylphenyl)-6-methylpyridine-2,3-dicarboximide 3.1 g (18.61 mmol) of the compound from example 4 were added to 2.9 g (17.7 mmol) of 6-methylpyridine-2,3-dicarboxylic anhydride and, with warming to 170° C., the mixture was stirred for a total of 8 h as a melt. After cooling, the residue was taken up in methylene chloride, and the solution was treated with active carbon and magnesium sulfate. After filtering off with suction, the filtrate was chromatographed on silica gel, 1.3 g (24.4% of theory) of the title compound being obtained after concentration as beige crystals of m.p. 173–176° C.

EXAMPLE 12

3-Chloro-6-methylisatoic anhydride 184 g (0.94 mol) of 3-chloro-6-methylisatin were introduced into a mixture of 750 ml of glacial acetic acid and 10 ml of conc. sulfuric acid and warmed to 70° C. with stirring. 145 ml (1.279 mol) of 30% strength hydrogen peroxide were then added in the course of 30 min at the same temperature and the mixture was stirred at 70 to 75° C. for 2 h. The precipitate was filtered off with suction after cooling, washed with water and dried. 146.6 g (73.7% of theory) were obtained as a beige powder of m.p. 248–250° C.

EXAMPLE 13

3-(6-chloro-2-cyano-3-methylphenyl)aminocarbonyl-6-methyl-pyridine-2-carboxylic acid N-n-propylamide 0.46 g (7.699 mmol) of n-propylamine was added with stirring at 22° C. to a mixture of 0.6 g (1.92 mmol) of the compound from example 11 in 30 ml of tetrahydrofuran and stirred for 12 h. The reaction mixture was concentrated in vacuo and the residue was stirred with diisopropyl ether/diethyl ether 20:1. After filtering off with suction and drying, 0.6 g (82.4% of theory) of the title compound were obtained as colorless crystals of m.p. 129–131° C.

EXAMPLE 14

3-Chloro-6-methylisatin a) 984 g (6.0 mol) of hydroxylammonium sulfate were added in portions with stirring at 22° C. to a mixture of 343 g (2.0 mol) of 2-chloro-5-methylaniline in 4 l of water. 124.5 g (1.22 mmol) of 96% strength sulfuric acid and 295 g (2.0 mol) of choral were then successively added dropwise with stirring in the course of 20 min in each case and the mixture was then stirred at 50° C. for 1 h. After cooling to 22° C., a pH of 1.8 was set by addition of 1.2 l of 20% strength sodium hydroxide solution. After standing overnight, the mixture was extracted with methylene chloride.

b) 3-Chloro-6-methylisatin 36.9 g (0.173 mol) of the compound from 14a were introduced in a mixture of 185.2 g (1.89 mol) of conc. sulfuric acid and 12.3 g of ice with stirring at 22 to 70° C. and stirred at 80° C. for 3 h. The reaction mixture was cooled to 30° C. and stirred into 3 l of ice water. The deposited precipitate was filtered off with suction, washed with water and dried, 26.3 g (73% of theory) of the title compound of m.p. 236–238° C. being obtained.

EXAMPLE 15

Methyl 2-amino-3-chloro-6-methylbenzoate 28.8 g (0.16 mol) of 30% strength sodium methoxide were added with stirring at 22° C. in the course of 10 min to a suspension of 25 g (0.128 mol) of the compound from example 14b. After cooling to 0° C., 10.9 g (0.16 mol) of 50% strength hydrogen peroxide were then added in the course of 30 min with stirring at 0 to 5° C. and the mixture was stirred at 22° C. for 1 h. The reaction mixture was neutralized by addition of a 1 molar solution of hydrogen chloride in ether and concentrated in vacuo. The residue was partitioned between methylene chloride and water, and the organic phase was washed a further 2× with dilute sodium hydrogen carbonate solution. The organic phase was dried over magnesium sulfate, filtered with suction through neutral alumina and concentrated. 17.7 g (69.4% of theory) of the title compound were obtained as a colorless oil of $n_D^{23}$=1.5761.

We claim:

1. A substituted aniline compound of the formula 1

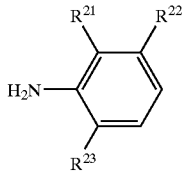

in which the variables $R^{21}$, $R^{22}$ and $R^{23}$ have the following meanings:

$R^{21}$ is a $C_1$–$C_3$-alkoxymethyl, $C_1$–$C_3$-alkoximinomethyl, $C_1$–$C_3$-alkoxycarbonyl, CN, $C_1$–$C_3$-alkyl;

$R^{22}$ is Cl, Br, $C_1$–$C_3$-alkyl;

$R^{23}$ is hydrogen, $C_1$–$C_3$-alkoxymethyl, $C_1$–$C_3$-alkoxycarbonyl, CN, Cl, Br, $C_1$–$C_3$-alkyl;

where at least one of the radicals $R^{21}$ or $R^{23}$ is $C_1$–$C_3$-alkoxycarbonyl or a functional derivative thereof or $C_1$–$C_3$-alkoxymethyl;

$R^{23}$ can not be hydrogen and $R^{22}$ and $R^{23}$ can not have the same meaning if $R^{21}$ is $C_1$–$C_3$-alkoxycarbonyl or CN;

$R^{22}$ does not have the same meaning as $R^{21}$ if $R^{21}$ is $C_1$–$C_3$-alkyl and $R^{23}$ is $C_1$–$C_3$-alkoxycarbonyl, and $R^{22}$ is not Cl if $R^{21}$ is $CH_3$ and $R^{23}$ is $C_1$–$C_3$-alkoxycarbonyl, $R^{23}$ is not hydrogen if $R^{21}$ is $C_1$–$C_3$-alkoxymethyl, or the salts thereof, with the exception of the compound of formula 1, where a) $R^{21}$ and $R^{23}$ are CN and $R^{22}$ is $CH_3$, and b) $R^{21}$ is CN, $R^{22}$ is $CH_3$ and $R^{23}$ is $CO_2CH_3$.

2. A compound of the formula 1 as defined in claim 1, in which $R^{21}$ is $C_1$–$C_3$-alkoxymethyl, $C_1$–$C_3$-alkoximinomethyl, $C_1$–$C_3$-alkoxycarbonyl, CN or $C_1$–$C_3$-alkyl;

$R^{22}$ is Cl, Br or $C_1$–$C_3$-alkyl and $R^{23}$ is $C_1$–$C_3$-alkoxymethyl.

3. A compound of the formula 1 as defined in claim 1, in which $R^{21}$ is $C_1$–$C_3$-alkoxymethyl or $C_1$–$C_3$-alkoximinomethyl;

$R^{22}$ is Cl, Br or $C_1$–$C_3$-alkyl and $R^{23}$ is H, $C_1$–$C_3$-alkoxymethyl, Cl, Br or $C_1$–$C_3$-alkyl.

4. A compound of the formula 1 as defined in claim 1, in which the variables $R^{21}$ to $R^{23}$ have the following meanings:

$R^{21}$ is $C_1$–$C_3$-alkoximinomethyl;

$R^{22}$ is Cl or Br;

$R^{23}$ is hydrogen.

5. A compound of the formula 1 as defined in claim 1, in which the variables $R^{21}$ to $R^{23}$ have the following meanings:

$R^{21}$ is $C_1$–$C_3$-alkoxycarbonyl or cyano;

$R^{22}$ and $R^{23}$, which are different from one another, are Cl, Br or $C_1$–$C_3$-alkyl, $R^{23}$ is furthermore $C_1$–$C_3$-alkoxycarbonyl.

6. A compound of the formula 1 as defined in claim 1, in which the variables $R^{21}$ to $R^{23}$ have the following meanings:

$R^{21}$ is $C_1$–$C_3$-alkoxymethyl or $C_1$–$C_3$-alkoximinomethyl;

$R^{22}$ is Cl, Br or $C_1$–$C_3$-alkyl;

$R^{23}$ is $C_1$–$C_3$-alkyl.

* * * * *